US009139515B2

(12) United States Patent
Hermsen et al.

(10) Patent No.: US 9,139,515 B2
(45) Date of Patent: Sep. 22, 2015

(54) SYNTHESIS OF R-BIPHENYLALANINOL

(75) Inventors: Petrus Johannes Hermsen, Echt (NL);
Peter Hans Ermann, Echt (NL); Peter Hans Riebel, Echt (NL); Michael Wolberg, Echt (NL); Andreas Hendrikus Maria De Vries, Echt (NL)

(73) Assignee: DPx Holdings B.V., Framingham, MA (US)

( * ) Notice: Subject to any disclaimer, the term of this patent is extended or adjusted under 35 U.S.C. 154(b) by 0 days.

(21) Appl. No.: 14/236,999

(22) PCT Filed: Aug. 16, 2012

(86) PCT No.: PCT/EP2012/066038
§ 371 (c)(1),
(2), (4) Date: Jun. 10, 2014

(87) PCT Pub. No.: WO2013/026773
PCT Pub. Date: Feb. 28, 2013

(65) Prior Publication Data
US 2014/0296559 A1    Oct. 2, 2014

(30) Foreign Application Priority Data

Aug. 19, 2011 (EP) .................................. 11178182

(51) Int. Cl.
| C07C 233/51 | (2006.01) |
| C07C 231/02 | (2006.01) |
| C07C 235/26 | (2006.01) |
| C07C 269/04 | (2006.01) |
| C07C 271/16 | (2006.01) |
| C07C 213/02 | (2006.01) |
| C07C 215/28 | (2006.01) |
| C07C 231/12 | (2006.01) |
| C07C 233/73 | (2006.01) |
| C07C 233/87 | (2006.01) |

(52) U.S. Cl.
CPC ............. *C07C 233/51* (2013.01); *C07C 213/02* (2013.01); *C07C 215/28* (2013.01); *C07C 231/12* (2013.01); *C07C 233/73* (2013.01); *C07C 233/87* (2013.01); *C07C 269/04* (2013.01); *C07C 271/16* (2013.01)

(58) Field of Classification Search
CPC .... C07C 233/51; C07C 231/02; C07C 235/26
USPC .......................................................... 560/27
See application file for complete search history.

(56) References Cited

U.S. PATENT DOCUMENTS

| 4,722,810 | A  | 2/1988  | Delaney et al. |
| 7,618,981 | B2 | 11/2009 | Qian et al. |
| 2007/0149516 | A1 | 6/2007 | Qian et al. |

FOREIGN PATENT DOCUMENTS

| CN | 1440416       |   | 9/2003  |       |            |
| CN | 101362708 A   |   | 2/2009  |       |            |
| CN | 101555211 A   |   | 10/2009 |       |            |
| CN | 101684077     |   | 3/2010  |       |            |
| EP | 0509442 A1    |   | 10/1992 |       |            |
| EP | 1980622 A1    |   | 10/2008 |       |            |
| WO | 9902153       |   | 1/1999  |       |            |
| WO | 9902153 A1    |   | 1/1999  |       |            |
| WO | 0204466 A2    |   | 1/2002  |       |            |
| WO | WO 02/04466   |   | 1/2002  |       |            |
| WO | 2005/014525 A2|   | 2/2005  |       |            |
| WO | 2005107762 A2 |   | 11/2005 |       |            |
| WO | 2007056469 A2 |   | 5/2007  |       |            |
| WO | 2008138561    |   | 11/2008 |       |            |
| WO | 2008138561 A1 |   | 11/2008 |       |            |
| WO | WO 2010/081410| * | 1/2010  | ............ | C07C 233/47 |
| WO | WO 2010/034236| * | 4/2010  | ............ | C07C 231/12 |
| WO | WO 2010/081410|   | 7/2010  |       |            |

OTHER PUBLICATIONS

International Search Report for PCT/EP2012/066038 mailed Jan. 14, 2013.
Written Opinion of the International Searching Authority mailed Jan. 14, 2013.
Klai et al., "Simple and Efficient Cleavage Reaction of the Boc Group in Heterocyclic Compounds" Journal of Heterocyclic Chemistry, vol. 41, 2004, pp. 57-60, XP-002666633.
Grayson et al., "A Tuneable Method for N-Debenzylation of Benzylamino Alcohols", Organic Letters, vol. 7, No. 12, May 14, 2005, pp. 2361-2364.
"The First Office Action" issued Oct. 27, 2014 from the State Intellectual Property Office of the People's Republic of China in connection with Chinese Patent Application No. 201280040329.X (6 pages).
Ksander, et al., "Dicarboxylic Acid Dipeptide Neutral Endopeptidase Inhibitors," J. Med. Chem., 1995, 38, pp. 1689-1700.
van den Berg, et al., "Monodentate Phosphoramidites: A Breakthrough in Rhodium-Catalysed Asymmetric Hydrogenation of Olefins," Adv. Synth. Catal., 2003, 345, pp. 308-323.
Knowles, et al., "Photochemical alkylation of glycine leading to phenylalanines," Tetrahedron Letters, 2000, 41#, pp. 7121-7124.
Green's Protective Groups in Organic Synthesis; Apr. 10, 2006; 4th Edition; pp. 724-725.
Green's Protective Groups in Organic Synthesis; Apr. 10, 2006; 4th Edition; pp. 814-815.
March's Advanced Organic Chemistry; Jan. 29, 2007; 6th Edition; pp. 1806-1811.

* cited by examiner

*Primary Examiner* — Kamal Saeed
*Assistant Examiner* — Janet L Coppins
(74) *Attorney, Agent, or Firm* — Pierce Atwood LLP; Raymond G. Arner

(57) ABSTRACT

This invention relates to a novel process for the synthesis of R-biphenylalaninol and to intermediate compounds that are formed in the process according to the invention, i.e. novel intermediates useful in the synthesis of R-biphenylalaninol. The invention also relates to R-biphenylalaninol, The process according to the invention, the intermediates to of R-biphenylalaninol and of R-biphenylalaninol are all useful in the synthesis of pharmaceutically active compounds.

7 Claims, No Drawings

SYNTHESIS OF R-BIPHENYLALANINOL

This application is the U.S. national phase of International Application No. PCT/EP2012/066038 filed 16 Aug. 2012 which designated the U.S. and claims priority to EP 11178182.9 filed 19 Aug. 2011, the entire contents of each of which are hereby incorporated by reference.

This invention relates to a novel process for the synthesis of R-biphenylalaninol and to intermediate compounds that are formed in the process according to the invention, i.e. novel intermediates useful in the synthesis of R-biphenylalaninol. The invention also relates to R-biphenylalaninol. The process according to the invention, the intermediates to of R-biphenylalaninol and of R-biphenylalaninol are all useful in the synthesis of pharmaceutically active compounds.

BACKGROUND OF THE INVENTION

The present invention relates to methods to prepare N-Boc protected biphenylalaninol, which is a key intermediate in the synthesis of pharmaceutically active compounds, e.g. neutral endopeptidase (NEP) inhibitors (see e.g. U.S. Pat. No. 4,722,810 and EP0059442.

R-biphenylalaninol is a novel compound. However, S-biphenylalaninol is mentioned and used in PCT-application WO9902153 (Table 1, page 25). However, the origin/preparation of this material is not disclosed. The synthesis of the racemic compound is described in CN101362708 (based on information disclosed in English abstract) The route described therein, however, is relatively long and requires an additional resolution step to obtain the desired enantiomerically enriched product. The S-enantiomer of Boc protected biphenyl alaninol has also been reported in U.S. Pat. No. 7,618,981; US2007056469; WO2005107762; WO2007056469; and WO2008138561. The typical synthetic method described therein to prepare the S-enantiomer of Boc protected biphenyl alaninol is based on the hydride reduction of Boc-protected biphenyl alanine which in turn can be prepared from enantiomerically pure biphenyl alanine using well established chemistry (*Greene's Protective Groups in Organic Synthesis*, 4th edition, page 725).

Several synthetic methods for preparation of D-biphenyl alanine have been reported. However, these are based on the use of expensive raw materials (D-Tyr; *J. Med. Chem.* 1995, 38, 1689) or rely on an (enzymatic) resolution of the corresponding racemic ester (EP1980622), which makes them less attractive from a commercial point of view. In addition, synthetic routes based on asymmetric hydrogenation of the N-acyl dehydroamino acid derivatives are known (*Adv. Synth. Cat.* 2003, 345, 308). The disadvantage of this approach is that the required hydrolysis of the N-acetyl group is time consuming and may give rise to erosion of enantiomeric excess.

Therefore, there is a strong need to develop inexpensive methods to prepare N-Boc protected biphenylalaninol. It is found that the present invention meets this objective and thus provides a process that is industrially advantageous.

SUMMARY OF THE INVENTION

This invention provides methods for preparing N-Boc protected biphenylalaninol of formula 5. The process according to the present invention is summarized in scheme 1. By reacting biphenyl formaldehyde with N-benzoylglycine and an anhydride a compound of formula 1 is obtained. Said compound is next converted into a compound of formula 2. Asymmetric hydrogenation of the latter compounds yields a compound of formula 3, which can be converted into a compound of formula 4. Hydrogenolysis and subsequent N-Boc protection yields the desired compound 5.

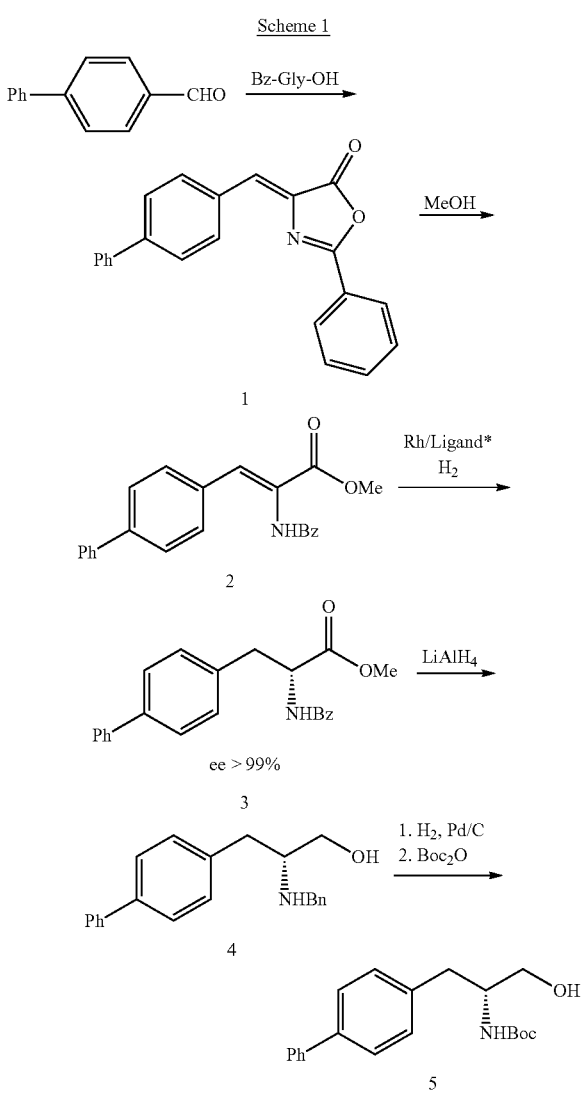

In the present application, the following abbreviations have been used: Boc=butoxycarbonyl, Bz=benzoyl with formula $C_6H_5C(O)$— and Bn=benzyl with formula $C_6H_5CH_2$—.

Substrate 2 can be asymmetrically hydrogenated to the target compound 3 with hydrogen in the presence of catalytically active, optically active rhodium or iridium complexes. The catalytically active complex used is preferably a rhodium complex formed by reaction of an Rh(I) complex with an optically active enantiomerically enriched chiral monodentate phosphoramidite ligand. The synthesis of such ligands, the use, the conditions for use and numerous examples of such ligands are described in WO02/04466, which is hereby incorporated by reference.

The catalytically active, optically active complexes for the asymmetric hydrogenation can be represented by the formula $ML_aX_bS_c$, where M is a transition metal, to be chosen from rhodium and iridium, L is an enantiomerically enriched chiral monodentate phosphoramidite ligand having the formula (VI),

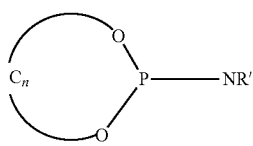
(VI)

where $C_n$ together with the two O-atoms and the P-atom forms a substituted or non-substituted ring with 2-4 C-atoms, $R^1$ and $R^2$ each independently stand for H, an optionally substituted alkyl, aryl, aralkyl or alkaryl group, or may form a (heterocyclic) ring together with the N-atom to which they are bound, X is a counter ion and S is a ligand, a ranges from 0.5 to 3, b and c each independently range from 0 to 2. Preferably $R^1$ and $R^2$ each independently represent an alkyl group, for instance an alkyl group with 1-6 C-atoms, in particular 1-3 C-atoms, most preferably $C_1$ and $C_2$ represent a methyl group. The alkyl, aryl, aralkyl and alkaryl groups preferably have 1-20 C-atoms and can optionally be substituted with for instance one or more hydroxy, alkoxy, nitrile or carboxylic ester groups, or halogens. $R^1$ and/or $R^2$ may be part of a polymeric backbone.

The catalyst according the formula $ML_aX_bS_c$ may be neutral, anionic or cationic. The catalyst may consist of a preformed complex having the formula $ML_aX_bS_c$. These complexes can be prepared by reacting the chiral ligand with a catalyst precursor. Preferably, however, the catalyst is formed in situ by adding the chiral ligand to a solution of a catalyst precursor which may contain a ligand that is easily removed by hydrogenation. The amount of optically active ligand to be added for example may range from 0.5 to 5, preferably from 1 to 3.5, equivalents relative to the metal. Preferably a small excess of optically active ligand is applied relative to the desired amount of optically active ligand in the catalyst. The optimum ratio of optically active ligand to metal in the catalyst may differ per optically active ligand and per metal and can readily be determined by means of experiments.

In the chiral ligand L of formula (I) $C_n$ and/or $R^1$ and/or $R^2$ are chiral or are part of a chiral entity. $C_n$ preferably represents a chiral substituted $C_4$ chain (chain with 4 optionally substituted C-atoms), of predominantly one configuration, for example with an enantiomeric excess larger than 95%, in particular larger than 99%, more in particular larger than 99.5%. Preferably $C_n$ together with the two O-atoms and the P-atom forms a 7-membered ring with 4 C-atoms which 2 by 2 form part of an aryl group or a naphthyl group. Some examples of suitable chiral ligands according to the invention are the following:

1

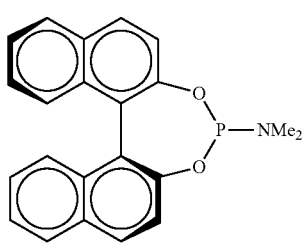

2

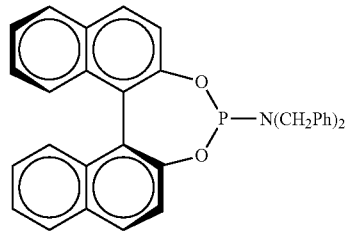

3

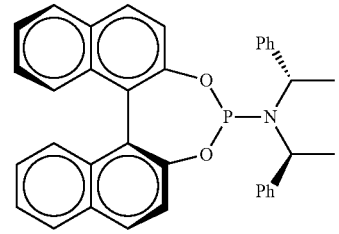

4

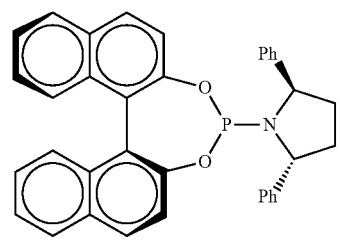

5

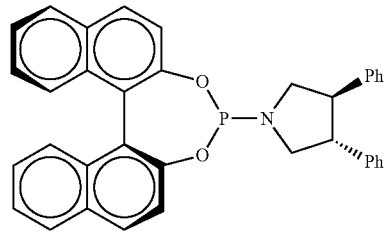

6

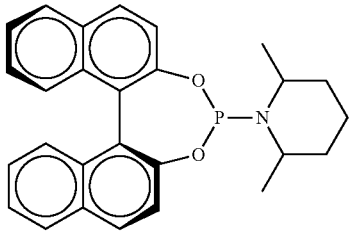

2a

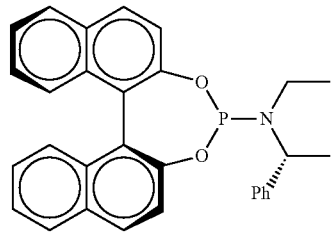

-continued
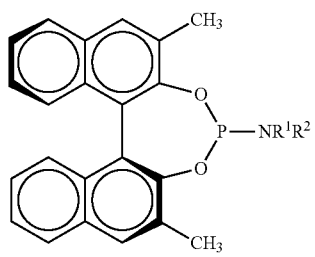
(R¹ and R² see text above)
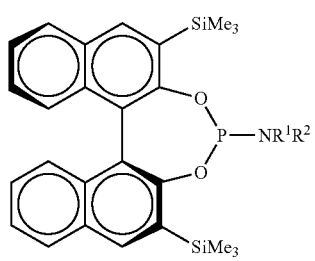
(R¹ and R² see text above)
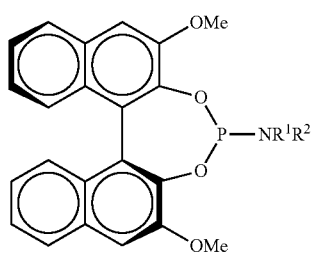
(R¹ and R² see text above)
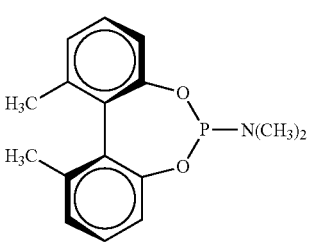
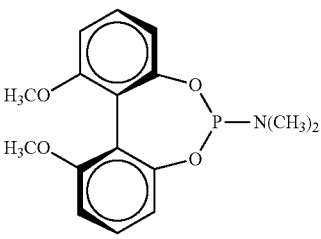
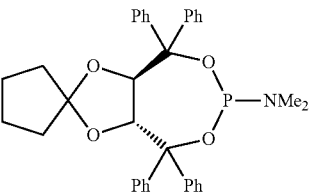
-continued
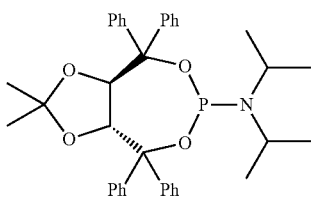
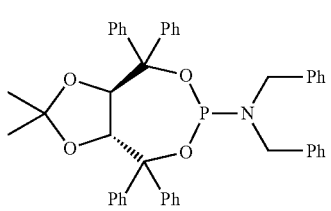
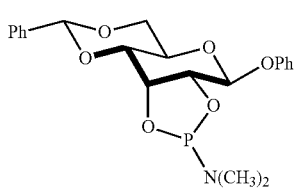
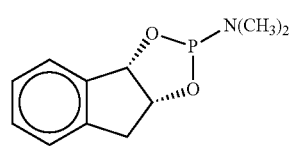
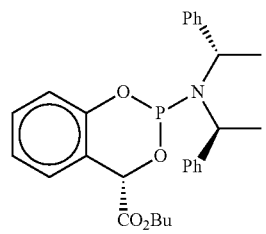
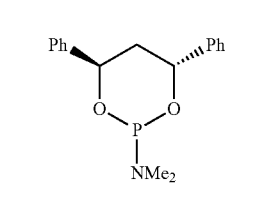
(R¹, R² see text above)
It will be understood that where one enantiomer is represented, the other enantiomer is similarly applicable.

Thus, the process according to the invention is a process for preparing a compound of formula I:

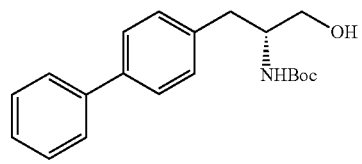

which process comprises the steps of:
a) asymmetrically hydrogenating a compound of formula II, wherein R=H, a linear or branched alkyl, an arylalkyl or aryl group in the presence of a catalytically active, optically active metal complex

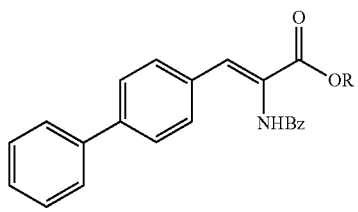

to give a compound of formula III

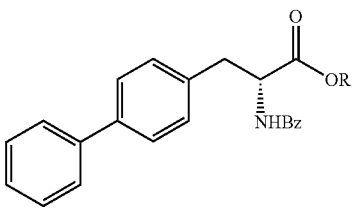

b) followed by reducing compound III to give a compound of formula IV

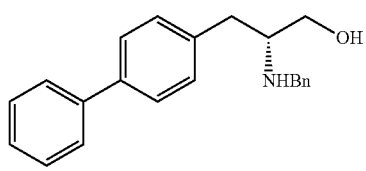

c) followed by hydrogenolysing compound IV to give a compound of formula V

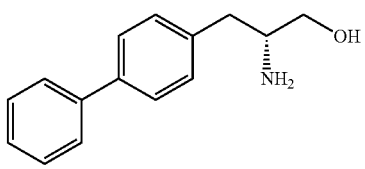

d) followed by Boc-protection of compound V to give the compound of formula I.

e) optionally isolating the compound of formula I

Many different R groups may be used, as long as they do not comprise any groups that interfere with the reactions that have to take place to synthesize any one of compounds III or IV. In a preferred embodiment of the process according to the invention, the R-groups will be either H or a $C_1$-$C_{12}$ linear or branched alkyl, a $C_1$-$C_{12}$ arylalkyl or $C_1$-$C_{12}$ aryl, wherein the aryl rings may optionally comprising hetero atoms, such as e.g. N and O, and wherein the R-group may optionally be substituted. Suitable substituents are known to a person skilled in the art, and will be chosen such that they will not interfere with the desired reaction taking place. R preferably is H or a $C_1$-$C_4$ alkyl group.

In a preferred embodiment of the process according to the invention, step c) and d) are combined by performing the hydrogenolysis in the presence of $Boc_2O$ to provide compound I directly. With this process the number of steps is advantageously reduced and isolation of intermediate V is avoided.

The asymmetric hydrogenation of 2 is advantageously carried out at a temperature of 20° C. to 200° C. and a hydrogen pressure of 1 to 200 bar. The molar ratio of catalyst to substrate is advantageously 1:1000 to 1:5000, preferably 1:1000 to 1:2000. Examples of suitable solvents for the asymmetric hydrogenation are esters such as ethyl acetate, chlorinated solvents such a dichloromethane or ethers such as tetrahydrofuran. Preferably tetrahydrofuran is used.

The conversion of ester 3 to amino alcohol 4 can be achieved using commonly known reagents for the reduction of esters and amides such as lithium aluminum hydride or borane (*March Advance Organic Chemistry, $6^{th}$ edition* page 1806 and 1841). This can be done in two separate steps but preferably in a singles step using a reagent which is known to reduce both moieties such as lithiumaluminum hydride.

Debenzylation of compound 4 can be achieved through commonly known techniques, such as hydrogenolysis using hydrogen and a palladium catalyst (*Greene's Protective Groups in Organic Synthesis, $4^{th}$ edition*, page 814). Boc-protection of the thus obtained amino alcohol can be achieved using standard techniques (*Greene's Protective Groups in Organic Synthesis, $4^{th}$ edition*, page 725).

The metal-ligand catalyst complex according to the invention is preferably catalytically active, optically active metal complex that is formed from a Rh(I) complex and an enantiomerically enriched optically active phosphoramidite monodentate ligand. Most preferably, the phosphoramidate ligand is (S)-1-(dinaptho[2,1-d:1',2'-f][1,3,2]dioxaphosphepin-4-yl)piperidine (S-PiPhos)

The invention also relates to a compound of formula II

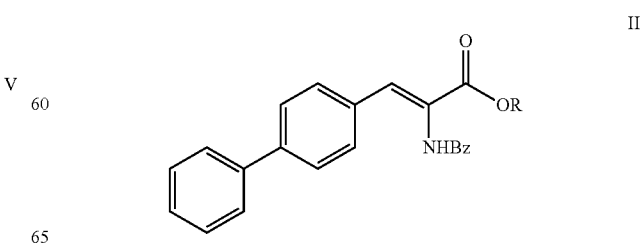

The invention also relates to a compound of formula III

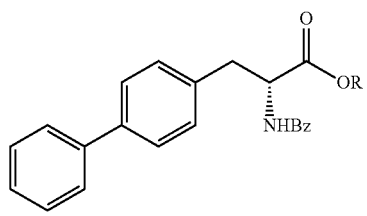

III

The invention also relates to a compound of formula IV

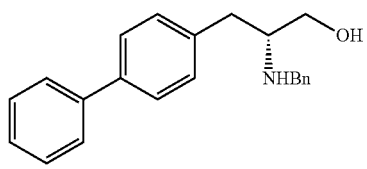

IV

The invention also relates to a compound of formula V

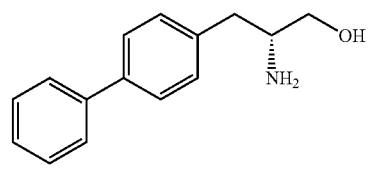

V

All compounds according to the invention are preferably substantially pure. In the framework of this invention, substantially pure is define as comprising less than 2 wt % of the S-isomer, more preferably comprising less than 1 wt %, and most preferably less than 0.5 wt % S-isomer. Preferably, the compounds according to the invention are optically pure compounds.

It should be noted that the synthesis of a racemic mixture of a compound according to formula III with R=methyl has been reported in *Tetrahedron Lett.* 2000, 7121, and with R=ethyl in CN101555211. The optically pure compound is, however, not described.

EXAMPLES

Example 1 a: Synthesis of Compound 3

The catalyst was prepared from bis(1,5-cyclooctadiene) rhodium(I) tetrafluoroborate (7.5 mg; 20 µmol) and (S)-1-(dinaptho[2,1-d:1',2'-f][1,3,2]dioxaphosphepin-4-yl)piperidine (S-PiPhos) (17.6 mg; 44 µmol) in $CH_2Cl_2$. Of this solution 500 µl was added to a solution of 360 mg of 2 in 5 ml of $CH_2Cl_2$. The thus obtained mixture was hydrogenated (25 bar $H_2$; 25° C.) until full conversion was reached (based on HPLC and $^1H$ NMR), providing compound 3 is quantitative yield (e.e. >99.5%, determined by chiral HPLC: Chiralpak IA-3; n-heptane:ethanol 85:15 v/v; 30° C., 1 mL/min).

| Solvent | S/C | $H_2$ pressure (bar) | T (° C.) | e.e. (%) |
| --- | --- | --- | --- | --- |
| THF | 500 | 25 | 25 | >99.5 |
| EtOAc | 500 | 25 | 25 | 99.4 |
| $CH_2Cl_2$ | 500 | 25 | 25 | 99.6 |
| $CH_2Cl_2$ | 1000 | 25 | 25 | 98.5 |
| THF | 1000 | 10 | 25 | 99.86 |
| 2-Me THF | 1000 | 10 | 25 | 99.92 |
| 2-Me THF | 1000 | 25 | 25 | 99.90 |
| $CH_2Cl_2$ | 1000 | 10 | 25 | 99.95 |

Example 1b

Autoclave Run at S/C=3000 in THF

Catalyst preparation: $Rh(NBD)_2BF_4$ (94.0 mg; 0.25 mmol) was dissolved in anhydrous and oxygen free dichloromethane (5 mL). To this solution was added (S)-1-(dinaptho[2,1-d:1', 2'-f][1,3,2]dioxaphosphepin-4-yl)piperidine (S-PiPhos) (201 mg; 0.50 mmol) portionwise. The color changed slowly to orange. After stirring for 1 h, the catalyst was precipitated by addition of dry and oxygen free n-heptane (10 mL). The precipitate was filtered off, washed with dry and oxygen free n-heptane, dried under reduced pressure, yielding 278 mg catalyst.

An autoclave of 200 mL was charged with 2 (36.25 g; 101 mmol), the catalyst (36 mg; 33 µmol); S/C=3000) and THF (120 mL) under nitrogen. Then, the reactor was pressurized to 30 bars and stirred for 16 h. The reactor was depressurized, vented with nitrogen and the volatiles were removed in vacuo resulting in 36.4 g, 100%) product with an e.e. >99%.

Example 2

Synthesis of Compound 4

To a dried 50 ml round bottom flask were added 1029 mg (2.87 mmol) of 3 and 10 ml of dry THF. To the obtained solution, $LiAlH_4$ was added portion wise (total 290 mg; 7.63 mmol). The reaction mixture was subsequently heated to reflux and stirred for 2 hours. After cooling to 20° C. the reaction was quenched by the addition of THF/water (3:1). The obtained mass was diluted with water (2 ml) and THF (10 ml). The precipitated salts were removed by filtration and the filtrate was concentrated in vacuo providing compound 4 is quantitative yield.

Example 3

Synthesis of Compound 5

125 mg of compound 4, 50 mg of Pd/C (Escat 1961; BASF) and 172 mg $Boc_2O$ in THF (5 ml) were hydrogenated for 18 hours (30° C., 5 bar). The catalyst was removed by filtration and the filtrate concentrated in vacuo. Upon trituration of the oily residue with $CHCl_3$ compound 5 crystallized. (e.e. >99%).

The invention claimed is:

1. A process for preparing a compound of formula I

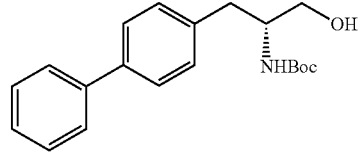

wherein Boc=butoxycarbonyl, which process comprises the steps of:

a) asymmetrically hydrogenating a compound of formula II

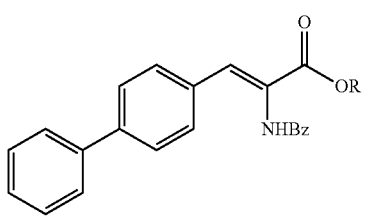

wherein R=$C_1$-$C_{12}$ linear or branched alkyl, $C_1$-$C_{12}$ arylalkyl or $C_1$-$C_{12}$ aryl, wherein the aryl rings may optionally comprise hetero atoms, wherein R may optionally be substituted, wherein Bz=benzoyl, in the presence of a catalytically active, optically active metal complex to give a compound of formula III

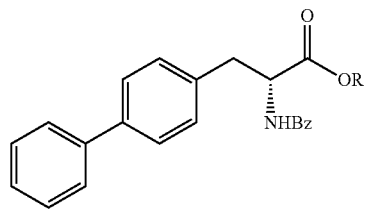

b) followed by reducing compound III to give a compound of formula IV

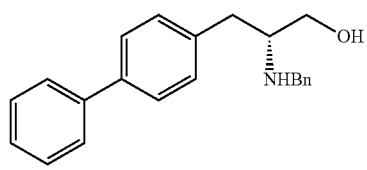

wherein Bn=benzyl, c) followed by hydrogenolysing compound IV to give a compound of formula V

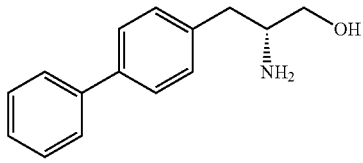

d) followed by Boc-protection of compound V to give the compound of formula I, e) optionally isolating the compound of formula I, wherein step c) and d) are combined by performing the hydrogenolysis in the presence of $Boc_2O$ to provide compound I directly.

2. The process of claim 1 wherein the catalytically active, optically active metal complex is formed from a Rh(I) complex and an optically active enantiomerically enriched phosphoramidite monodentate ligand.

3. The compound of formula IV

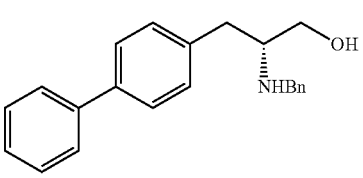

wherein Bn=benzyl.

4. The compound of formula V

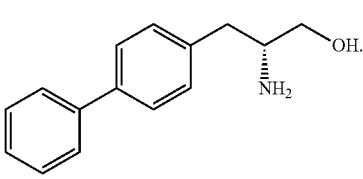

5. A process for preparing a compound of formula I

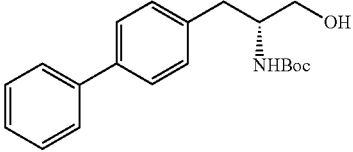

wherein Boc=butoxycarbonyl, which process comprises the steps of
 a) hydrogenolysing compound IV

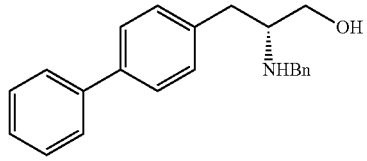
IV wherein Bn=Benzyl
to give a compound of formula V

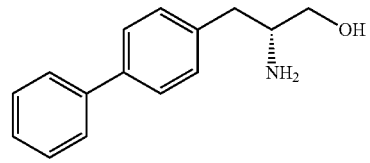
V b) followed by Boc-protection of compound V to give the compound of formula I,
c) optionally isolating the compound of formula I.

6. A process for preparing a compound of formula I

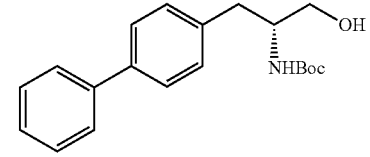
I wherein Boc=butoxycarbonyl, which process comprises the steps of
 a) Boc-protecting of compound V

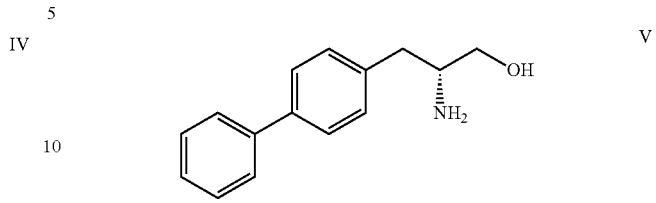
V to give the compound of formula I,
b) optionally isolating the compound of formula I.

7. A process for synthesizing of a pharmaceutically active compound by converting a compound of formula V

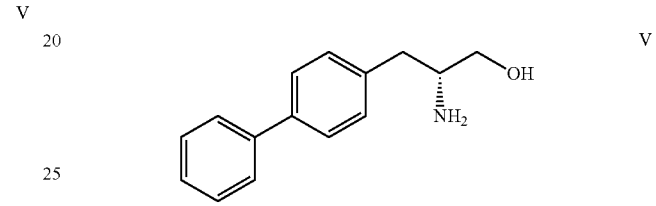
V to a compound of formula I

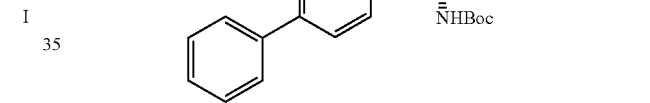
I and subsequently converting the compound of formula I into the pharmaceutically active compound.

* * * * *